(12) United States Patent
Yabe et al.

(10) Patent No.: US 10,939,811 B2
(45) Date of Patent: Mar. 9, 2021

(54) LIGHT SOURCE DEVICE FOR ENDOSCOPE AND ENDOSCOPE SYSTEM

(71) Applicant: OLYMPUS CORPORATION, Tokyo (JP)

(72) Inventors: Yusuke Yabe, Chofu (JP); Satoshi Tanaka, Hachioji (JP); Tomoya Takahashi, Hachioji (JP); Masaaki Watanabe, Hachioji (JP); Susumu Hashimoto, Hachioji (JP); Yasuo Komatsu, Yokohama (JP); Manabu Yajima, Hachioji (JP); Akihiko Mochida, Hachioji (JP); Koji Omori, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 419 days.

(21) Appl. No.: 15/951,238

(22) Filed: Apr. 12, 2018

(65) Prior Publication Data

US 2018/0228354 A1 Aug. 16, 2018

Related U.S. Application Data

(63) Continuation of application No. PCT/JP2016/078048, filed on Sep. 23, 2016.

(30) Foreign Application Priority Data

Oct. 14, 2015 (JP) .............................. JP2015-203003

(51) Int. Cl.
*A61B 1/06* (2006.01)
*A61B 1/05* (2006.01)
(Continued)

(52) U.S. Cl.
CPC .......... *A61B 1/0661* (2013.01); *A61B 1/0638* (2013.01); *A61B 1/0646* (2013.01);
(Continued)

(58) Field of Classification Search
CPC ............. G02B 23/2469; A61B 1/0661; A61B 1/0638; A61B 1/0646; A61B 1/0653;
(Continued)

(56) References Cited

U.S. PATENT DOCUMENTS

2002/0175993 A1 11/2002 Ueno et al.
2004/0143157 A1 7/2004 Doguchi et al.
(Continued)

FOREIGN PATENT DOCUMENTS

EP 1099405 A1 5/2001
EP 1258220 A2 11/2002
(Continued)

OTHER PUBLICATIONS

International Search Report dated Nov. 15, 2016 issued in PCT/JP2016/078048.

*Primary Examiner* — Timothy J Neal
*Assistant Examiner* — William B Chou
(74) *Attorney, Agent, or Firm* — Scully, Scott, Murphy & Presser, P.C.

(57) ABSTRACT

A light source device for endoscope includes a rotational body configured to rotate with a rotational axis as a center; a fluorescent body arranged in a predetermined area of the rotational body and configured to generate fluorescence by excitation light being radiated; an illuminating portion capable of selectively radiating excitation light of a first quantity and excitation light of a second quantity which is larger than the first quantity to a fluorescent body; and a control portion configured to switch between a first state of radiating the excitation light of the first quantity to the
(Continued)

fluorescent body arranged in a first area and a second state of radiating the excitation light of the second quantity to the fluorescent body arranged in a second area.

11 Claims, 4 Drawing Sheets

(51) Int. Cl.
*A61B 1/07* (2006.01)
*G02B 23/24* (2006.01)
*A61B 1/04* (2006.01)

(52) U.S. Cl.
CPC .......... *A61B 1/0653* (2013.01); *A61B 1/0669* (2013.01); *A61B 1/07* (2013.01); *G02B 23/2469* (2013.01); *A61B 1/043* (2013.01); *A61B 1/05* (2013.01)

(58) Field of Classification Search
CPC ......... A61B 1/0669; A61B 1/07; A61B 1/043; A61B 1/05
See application file for complete search history.

(56) References Cited

U.S. PATENT DOCUMENTS

| | | | | |
|---|---|---|---|---|
| 2006/0241496 | A1* | 10/2006 | Fengler | A61B 1/0638 600/476 |
| 2010/0073731 | A1* | 3/2010 | Takei | A61B 1/043 358/443 |
| 2010/0259656 | A1* | 10/2010 | Irion | A61B 1/0638 348/273 |
| 2011/0164249 | A1* | 7/2011 | Innami | G01N 21/645 356/326 |
| 2013/0012864 | A1* | 1/2013 | Kubo | A61B 1/041 604/20 |
| 2014/0012113 | A1* | 1/2014 | Kaku | A61B 5/1459 600/339 |
| 2015/0099932 | A1* | 4/2015 | Morimoto | A61B 1/0661 600/180 |
| 2015/0313517 | A1* | 11/2015 | Yamaguchi | A61B 1/043 600/335 |
| 2018/0042470 | A1* | 2/2018 | Tanaka | A61B 1/0646 |

FOREIGN PATENT DOCUMENTS

| | | |
|---|---|---|
| JP | 2001-029313 A | 2/2001 |
| JP | 2002-336196 A | 11/2002 |
| JP | 2005-312551 A | 11/2005 |
| JP | 2013-215435 A | 10/2013 |
| JP | 2015-116378 A | 6/2015 |
| JP | 2015-119836 A | 7/2015 |
| WO | WO 00/69324 A1 | 11/2000 |
| WO | WO 2015/016013 A1 | 2/2015 |

* cited by examiner

LIGHT SOURCE DEVICE FOR ENDOSCOPE AND ENDOSCOPE SYSTEM

CROSS REFERENCE TO RELATED APPLICATION

This application is a continuation application of PCT/JP2016/078048 filed on Sep. 23, 2016 and claims benefit of Japanese Application No. 2015-203003 filed in Japan on Oct. 14, 2015, the entire contents of which are incorporated herein by this reference.

BACKGROUND OF THE INVENTION

1. Field of the Invention

The present invention relates to a light source device for endoscope which is equipped with a rotational body provided with a fluorescent body configured to cause light in a predetermined wavelength range to be emitted upon receiving light radiated from an illuminating portion, and an endoscope system.

2. Description of the Related Art

Conventionally, endoscopes configured having an elongated insertion portion are widely used, for example, in a medical field, an industrial field and the like. Among the endoscopes, a medical endoscope used in the medical field is configured so that it is possible to insert the insertion portion into a subject, for example, a body cavity of a living body to observe an organ or the like and, when necessary, perform various treatments for the organ using a treatment instrument inserted into a treatment instrument insertion channel provided for the endoscope. Further, an industrial endoscope used in the industrial field is configured so that it is possible to insert the insertion portion into an inside of an object, for example, a device such as a jet engine and factory piping or mechanical equipment, perform observation, inspection and the like of a state in the object, for example, a state of a flow and corrosion.

An environment under which such kind of endoscope is used is, for example, an inside of a body cavity of a living body or an inside of piping of mechanical equipment where it may be dark without ambient light. As a configuration for acquiring an endoscopic image even in such a case, an endoscope system which is configured being provided with a light source device for radiating illuminating light externally forward from a distal end portion of the endoscope is well known.

Among light source devices in such a form which are applied to conventional endoscope systems, some are configured to be capable of emitting not only ordinary white illuminating light but also illuminating lights with different wavelengths according to uses of endoscopes. Various kinds of light source devices, such as a light source device configured to, using an excitation light source (the illuminating portion) configured to emit excitation light (laser) and a fluorescent body wheel configured to rotation-drive a fluorescent body configured to emit fluorescence upon receiving the excitation light, radiate the excitation light as illuminating light, have been proposed and put to practical use.

In an conventional endoscope system using a light source device of this kind, there is a problem that a position of radiating the excitation light to the fluorescent body provided on the rotational body cyclically changes, for example, due to a rotational body rotating mechanism (a rotational shake of a rotational axis, mounting accuracy of the rotational body or the like), and cyclic light quantity fluctuations occur in the fluorescence emitted from the fluorescent body.

Therefore, for example, in a light source device for endoscope and an endoscope system disclosed by Japanese Patent Application Laid-Open Publication No. 2015-116378, in a light source configured to radiate excitation light to a fluorescent body wheel (a rotational body) to cause fluorescence to be generated, in order to suppress light quantity fluctuations accompanying rotation of the fluorescent body wheel, light quantity fluctuations data showing a relationship between a radial-direction rotation position on the fluorescent body wheel (the rotational body) and a quantity of light is acquired in advance, and a quantity of the excitation light is controlled using such data (anti-phase control or the like).

SUMMARY OF THE INVENTION

A light source device for endoscope of an aspect of the present invention includes: a rotational body configured to rotate with a rotational axis as a center; a fluorescent body arranged in an area on the rotational body, the area having a predetermined radius with the rotational axis as a center, and configured to generate fluorescence by excitation light being radiated; an illuminating portion capable of selectively radiating excitation light a quantity of which is a first quantity of light and excitation light a quantity of which is a second quantity of light which is a quantity of light larger than the first quantity of light to the fluorescent body; and a control portion configured to control a radiation position to which the excitation light is radiated so as to switch between a first state of radiating the excitation light the quantity of which is the first quantity of light to the fluorescent body arranged in an area having a first radius from the rotational axis and a second state of radiating the excitation light the quantity of which is the second quantity of light to the fluorescent body arranged in an area having a second radius from the rotational axis that is longer than the first radius.

An endoscope system of an aspect of the present invention is provided with the above light source device for endoscope and an endoscope.

BRIEF DESCRIPTION OF THE DRAWINGS

FIG. 5 is a graph showing a relationship between a making current (I) to a semiconductor laser LD (an illuminating portion) and a quantity of emitted excitation light (Q)

in a light source device for endoscope of a second embodiment of the present invention.

DETAILED DESCRIPTION OF THE PREFERRED EMBODIMENTS

The present invention will be described below by embodiments shown in drawings. Each drawing used in the description below is schematic, and a dimensional relationship, reduced scale and the like of each member may be shown different for each component in order to show the component in a recognizable size on the drawing. Therefore, as for the number of components, shapes of the components, a ratio of sizes of the components, relative positional relationship among the respective components, and the like shown in each of the drawings, the present invention is not limited to forms shown in the drawing.

First Embodiment

Figure 1:
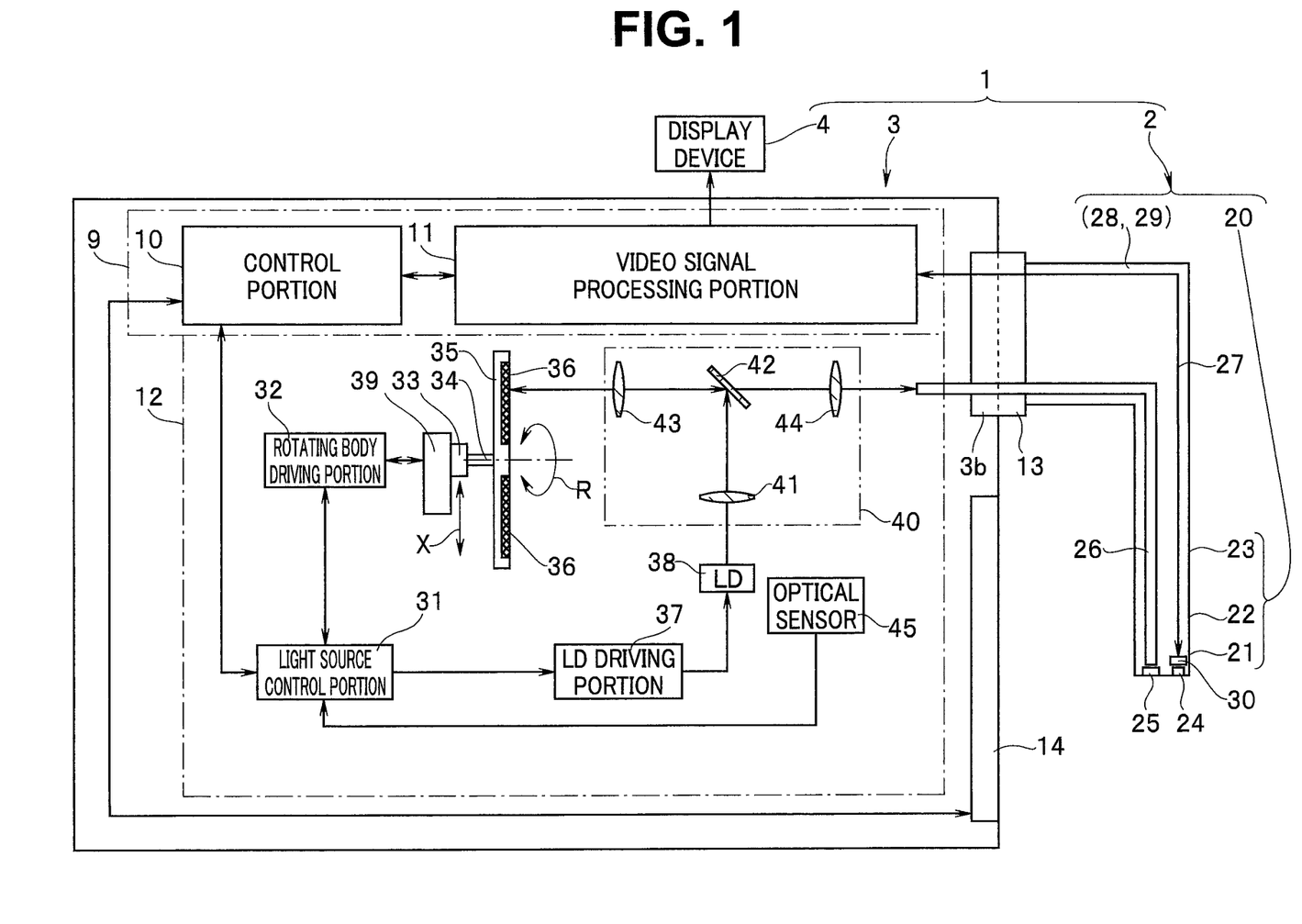
FIG. 1 is a block configuration diagram showing a schematic configuration of an endoscope system which includes a light source device for endoscope of a first embodiment of the present invention.

FIG. 1 is a block configuration diagram showing a schematic configuration of an endoscope system which includes a light source device for endoscope of a first embodiment of the present invention. First, an overall schematic configuration of the endoscope system which includes the light source device for endoscope of the present embodiment will be described using FIG. 1.

As shown in FIG. 1, an endoscope system 1 is mainly configured having an endoscope 2, a control unit 3 and a display device 4. The endoscope 2 is configured to be attachable to and detachable from a connector portion 3b (to be described later) of the control unit 3 via a connector 13 (to be described later).

Note that, as the endoscope 2 itself which is applied in the present embodiment, an endoscope which has been conventionally and commonly used to practice and spread can be applied as it is. Therefore, a configuration of the endoscope 2 itself is shown being simplified. As for each component portion also, detailed description is omitted; and only important configurations related to the present invention will be described.

The endoscope 2 is a component unit configured to, for example, with an inside of a body cavity as an observation target, pick up an image of the observation target object and output an image pickup signal. The endoscope 2 is configured having an elongated insertion portion 20 insertable into the body cavity, an operation portion 28 connectedly arranged on a proximal end side of the insertion portion 20, a universal cable 29 extending from the operation portion 28, the connector 13 provided at a distal end of the universal cable 29, and the like.

The insertion portion 20 forms an elongated tubular shape with a distal end portion 21, a bending portion 22 and a flexible tube portion 23 being connectedly arranged from the distal end side. The above distal end portion 21 is provided with an illumination lens 25, an image pickup objective lens 24 and the like.

The above illumination lens 25 is an optical lens configured to condense illuminating light transmitted from a light source unit 12 by a light guide 26 and emit the illuminating light forward from a front of the above distal end portion 21. Therefore, a distal end face of the light guide 26 configured to guide illuminating light for illuminating an observation target from the light source unit 12 (to be described later in detail) to a distal end of the insertion portion 20 is arranged on a rear end face of the above illumination lens 25. The light guide 26 is inserted through the insertion portion 20, the operation portion 28 and the universal cable 29 and connected to the light source unit 12 (to be described later) in the control unit 3 via the above connector 13 and the connector portion 3b. By such a configuration, illuminating light emitted from the light source unit 12 is supplied to the illumination lens 25 via the light guide 26 and emitted frontward from the endoscope 2 from the illumination lens 25. Thereby, a subject, which is an observation target object existing in an area facing a distal end face of the distal end portion 21 of the insertion portion 20 of the endoscope 2 is illuminated.

Further, the image pickup objective lens 24 is an optical lens configured to cause an optical image of the subject illuminated by the illuminating light from the above illumination lens 25 to be formed. The image pickup objective lens 24 is arranged, for example, adjoining to the above illumination lens 25 on the front of the above distal end portion 21. At an image forming position behind the image pickup objective lens 24, an image pickup unit 30 is arranged. The image pickup unit 30 is a component unit including an image pickup device (not shown) which is an electronic part configured to, upon receiving the optical image formed by the above image pickup objective lens 24, perform photoelectric conversion processing to generate an image pickup signal, and the like. Note that, as the above image pickup device (not shown), a photoelectric conversion device, for example, a CCD (charge coupled device) image sensor or a CMOS (complementary metal oxide semiconductor) type image sensor is applied. A signal line 27 extends toward a back of the insertion portion 20 from the above image pickup unit 30, and the signal line 27 is inserted through the insertion portion 20, the operation portion 28 and the universal cable 29 and connected to a video signal processing portion 11 (to be described later) in the control unit 3 via the above connector 13 and the connector portion 3b. By the configuration, an image pickup signal generated by the image pickup device of the image pickup unit 30 is transmitted to the video signal processing portion 11 via the signal line 27. Other components of the above endoscope 2 are almost similar to components of a conventional ordinary endoscope.

The control unit 3 is configured having a signal processing control unit 9 configured with a control portion 10 and the video signal processing portion 11, the light source unit 12 which is the light source device for endoscope, the connector portion 3b, an operation panel 14 and the like.

Note that, though a form of the signal processing control unit 9 and the light source unit 12 being configured in a same case is illustrated in the present embodiment, the signal processing control unit 9 and the light source unit 12 are not limited to such a form. For example, a form is also possible in which the signal processing control unit 9 and the light source unit 12 are separately configured and mutually connected via a cable.

The above connector portion 3b and the above operation panel 14 are component members provided on a front of the case of the above control unit 3. The above connector portion 3b is a connection portion configured to connect the above control unit 3 and the above endoscope 2 by the above connector 13 of the above universal cable 29 being fitted to the connector portion 3b. Further, the above operation panel 14 is a component portion configured with a circuit board or the like (not shown) having a plurality of various operation members for accepting operations by a user and configured to output respective predetermined instruction signals in response to the operations of the plurality of operation members.

The control portion 10 in the above signal processing control unit 9 is a control portion configured to comprehensively control the whole endoscope system 1. The control portion 10 is electrically connected to each component unit of the endoscope system 1 and performs various controls by appropriately outputting a predetermined control signal at a predetermined timing. Further, the control portion 10 is electrically connected to the above operation panel 14 so that an instruction signal from the above operation panel 14 is inputted. Upon receiving inputted various instruction signals, the control portion 10 appropriately controls corresponding component units.

Upon receiving an image pickup signal outputted from (the image pickup unit 30 of) the endoscope 2, the video signal processing portion 11 in the above signal processing control unit 9 performs processing for converting the image pickup signal to a predetermined video signal and outputs the video signal to the display device 4.

The display device 4 is a component unit for displaying an image corresponding to the video signal outputted from the video signal processing portion 11. As the display device 4, for example, an image receiver using a cathode-ray tube (CRT) or the like is applied in addition to a liquid crystal display (LCD) device, an organic electroluminescence (OEL) display device or the like.

The light source unit 12, which is the light source device for endoscope, is a component unit configured to supply illuminating light for illuminating an observation target to the above illumination lens 25 of the distal end portion 21 of the endoscope 2 via the light guide 26.

The light source unit 12 in the endoscope system 1 of the present embodiment is configured mainly with a light source control portion 31, a rotational body driving portion 32, a rotational body driving motor 33, a rotational body rotational axis 34, a fluorescent wheel 35 which is a rotational body, a fluorescent body 36, a light emission driving portion (abbreviated as an LD driving portion in FIG. 1) 37, a semiconductor laser LD (laser diode; abbreviated as LD in FIG. 1) 38 which is an illuminating portion, a rotational body shifting mechanism 39, an optical unit 40, an optical sensor 45 and the like.

The light source control portion 31 is a control portion configured to control the light source unit 12 under control of the control portion 10. In the present embodiment, the light source control portion 31 especially has a function of, for the fluorescent wheel 35 (a rotational body), performing control to change a position of radiating excitation light by the fluorescent body 36 in a radial direction of the fluorescent wheel 35 (the rotational body) with the rotational body rotational axis 34 as a center, though details will be described later.

The rotational body driving portion 32 is a component portion having a drive circuit for performing rotation control (speed control and the like) of the rotational body driving motor 33 (the fluorescent wheel 35) and shift/movement control of a rotational body unit (to be described later) including the fluorescent wheel 35 in a direction orthogonal to an axial direction of the rotational body rotational axis 34 of the rotational body shifting mechanism 39. The rotational body driving portion 32 is electrically connected to the above light source control portion 31 and is controlled by the above light source control portion 31.

The rotational body driving motor 33 is a rotary motor coupled with the fluorescent wheel 35 via the rotational body rotational axis 34. The rotational body driving motor 33 generates driving force for rotating the fluorescent wheel 35 around the rotational body rotational axis 34 in a direction of an arrow R in FIG. 1.

The rotational body shifting mechanism 39 is a mechanism portion for causing the fluorescent wheel 35 to shift and move in a direction orthogonal to the axial direction of the rotational body rotational axis 34 (a direction of an arrow X in FIG. 1). In short, the rotational body shifting mechanism 39 is a rotational body moving mechanism enabling the fluorescent wheel 35 (the rotational body) to move in the radial direction. Actually, the rotational body shifting mechanism 39 is configured to cause an assembly (the rotational body unit to be described later) configured with the above rotational body driving motor 33, the above rotational body rotational axis 34, the above fluorescent wheel 35 and the like to move in a predetermined direction (the X direction) as an integrated body.

The rotational body rotational axis 34 is a shaft member integrally fixed to a rotational center of the fluorescent wheel 35, which is a rotational body, and configured to cause the fluorescent wheel 35 to rotate.

The fluorescent wheel 35 is a rotational body which is formed in a thin disk shape and rotates with the above rotational body rotational axis 34 as the center. On one of disk surfaces (a surface which receives light radiated from the semiconductor laser LD 38 to be described later) of the fluorescent wheel 35, the fluorescent body 36 is provided.

The fluorescent body 36 is a light emitting body provided in an area on the above fluorescent wheel 35 (the rotational body), the area having a predetermined radius with the rotational body rotational axis 34 as the center, and configured to, when radiated light (excitation light) from the semiconductor laser LD 38 to be described later is radiated, get excited and emit fluorescence. Note that, though an example is shown in which the fluorescent body 36 is provided such that the fluorescent body 36 covers almost the whole of the one disk surface of the fluorescent wheel 35, as shown in FIG. 1, the fluorescent body 36 is not limited to the configuration example. For example, the fluorescent body 36 may be provided with a plurality of predetermined annular areas in the radial direction on one disk surface of the fluorescent wheel 35 and configured to separate the respective areas so that the above shift/movement of the above rotational body unit can be gradually performed.

The LD driving portion 37 is a component portion for, by being controlled via the light source control portion 31 under control of the control portion 10, generating a semiconductor laser LD drive current for drive-controlling the semiconductor laser LD 38 and supplying the drive current to the semiconductor laser LD 38 to cause light in a predetermined wavelength range to be emitted.

The semiconductor laser LD 38 is an illuminating portion configured to radiate excitation light. The radiated light (excitation light) radiated from the semiconductor laser LD 38 is configured to be radiated to the fluorescent body 36 by an action of the optical unit 40 (to be described later in detail). Note that the above semiconductor laser LD 38 (the illuminating portion) is configured so that a quantity of emitted light is variable. That is, the semiconductor laser LD 38 is configured to be capable of selectively radiating at least two kinds of quantities of excitation light, for example, excitation light the quantity of which is a first quantity of light and excitation light the quantity of which is a second quantity of light, the second quantity of light being larger than the first quantity of light.

The optical sensor 45 is a detector configured to detect a quantity of radiated light (excitation light) emitted from the above semiconductor laser LD 38 and output a result of the detection. The detection result of the optical sensor 45 is outputted to the light source control portion 31 and used to drive-control the rotational body driving portion 32. For example, the optical sensor 45 is provided with an output portion configured to output, from the detection result of the quantity of emitted excitation light the above semiconductor laser LD 38 (the illuminating portion) radiates, a control signal for controlling the quantity of light. The control signal for controlling the quantity of light is outputted to the light source control portion 31 by the output portion.

The optical unit 40 is configured having a lens 41, a dichroic filter 42, a lens 43 and a lens 44.

The above lens 41 is an optical lens configured to transmit radiated light (excitation light) from the semiconductor laser LD 38 and emit the radiated light to the dichroic filter 42.

The above dichroic filter 42 is a plate-shaped optical member having a function of, upon receiving radiated lights (excitation lights) from the semiconductor laser LD 38 which have been transmitted through the above lens 41, reflecting the radiated lights (excitation lights) toward the above fluorescent body 36 side, and, as described later, transmitting a light in a particular wavelength range among the radiated lights (fluorescence) from the fluorescent body 36 which have been transmitted through the lens 43. Therefore, the above dichroic filter 42 is arranged being tilted at an angle of 45 degrees relative to both of an optical axis of the above lens 41 and an optical axis of the above lens 43. In this case, a reflection plane of the dichroic filter 42 is arranged facing the above fluorescent body 36 side so that the radiated light (excitation light) from the semiconductor laser LD 38 can be reflected toward the above fluorescent body 36 side.

The lens 43 is an optical lens configured to transmit the radiated light (excitation light) from the semiconductor laser LD 38 reflected by the above dichroic filter 42 and guide the radiated light to the above fluorescent body 36 and to transmit radiated light (fluorescence) from the fluorescent body 36 and emit the radiated light toward the above dichroic filter 42 side.

The lens 44 is an optical lens configured to transmit the radiated light (fluorescence) from the above fluorescent body 36 which has traveled straight through the above lens 43 and the above dichroic filter 42 and emit the radiated light to a proximal end face of the light guide 26.

Note that, to describe the above briefly, in the light source unit 12 which is the light source device for endoscope of the present embodiment, a light emitting unit for emitting light in a predetermined wavelength range and transmitting the light to the light guide 26 is configured with the above rotational body unit (the rotational body driving motor 33, the rotational body rotational axis 34, the fluorescent wheel 35 (the rotational body) and the fluorescent body 36), an LD unit (the LD driving portion 37 and the semiconductor laser LD 38) and the optical unit 40 (41, 42, 43 and 44). On an assumption that other components of the above endoscope system 1 are almost similar to components of a conventional ordinary endoscope system, description of the components will be omitted.

Operation of the endoscope system 1 which includes the light source device for endoscope (the light source unit 12) of the present embodiment configured as described above will be described below.

Figure 2:
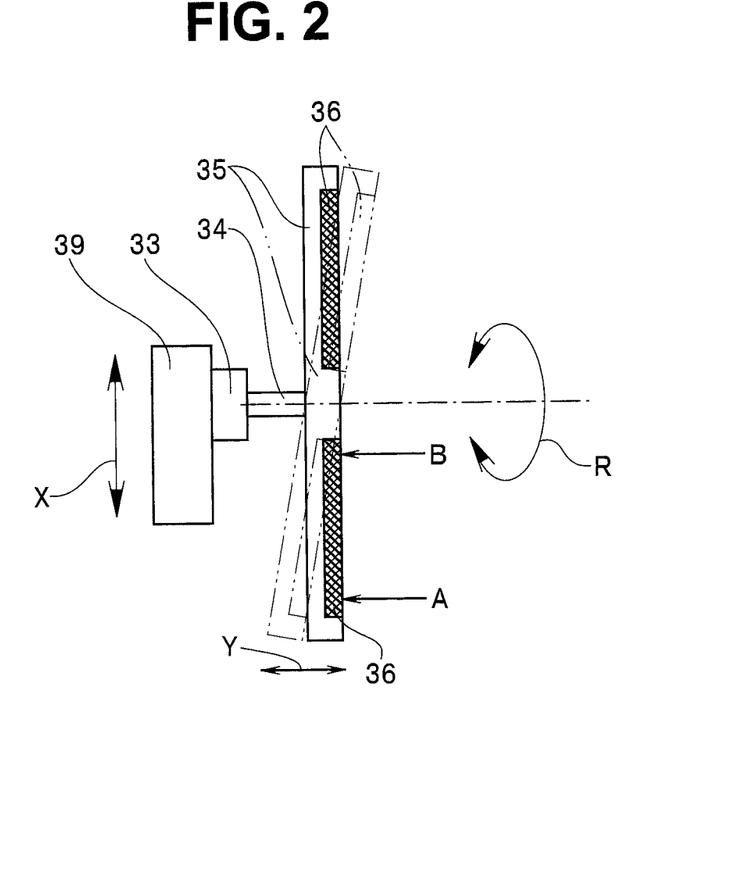
FIG. 2 is a main part enlarged block diagram enlargingly showing a rotational body unit and a rotational body shifting mechanism taken out from among component members of the light source device for endoscope (a light source unit) in FIG. 1.

FIG. 2 is a main part enlarged block diagram enlargingly showing the above rotational body unit (the rotational body driving motor 33, the rotational body rotational axis 34, the fluorescent wheel 35 (the rotational body) and the fluorescent body 36) and the rotational body shifting mechanism 39 taken out from among the component members of the light source unit 12 of the present embodiment.

The light source unit 12 of the present embodiment is configured to radiate radiated light (excitation light) from the semiconductor laser LD 38 (the illuminating portion) to the fluorescent body 36 provided on the fluorescent wheel 35 (the rotational body) to emit light in a predetermined wavelength range. When such a configuration is adopted, there is a possibility that a position of radiating radiated light (excitation light) from the semiconductor laser LD 38 (the illuminating portion) onto the fluorescent body 36 varies due to various mechanical factors such as planarity of a disk surface of the fluorescent wheel 35 on which the fluorescent body 36 is arranged, inclination of the disk surface based on accuracy of attaching the fluorescent wheel 35 to the rotational body rotational axis 34, and a rotational shake of the rotational body rotational axis 34. For example, in FIG. 2, a state in a case where inclination of the disk surface of the fluorescent wheel 35 (the rotational body) occurs is indicated by two-dot chain lines. At this time, if the fluorescent wheel 35 rotates around the rotational body rotational axis 34 (in a direction of an arrow R), rotational deflection of the fluorescent wheel 35 occurs in a direction of an arrow Y in FIG. 2.

Figure 3:
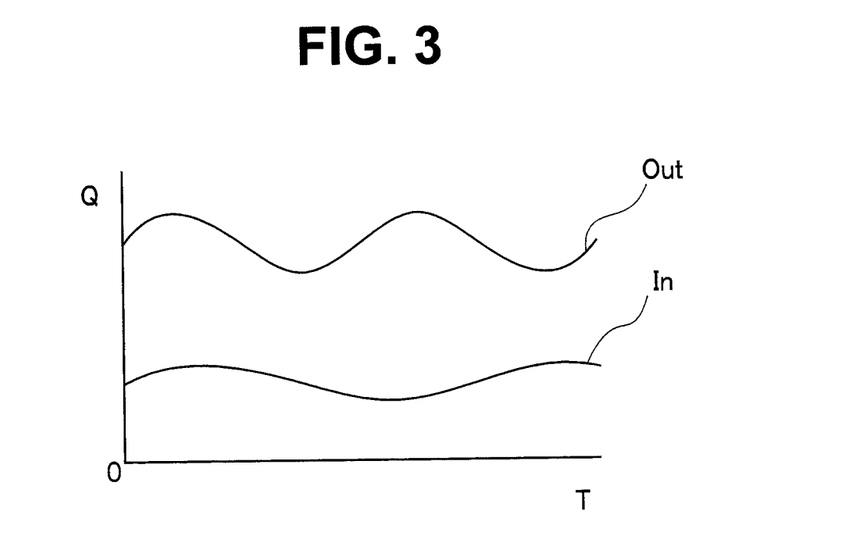
FIG. 3 is a graph showing chronological fluctuations in a quantity of radiated light (fluorescence) emitted from a fluorescent wheel (a rotational body) in the light source device for endoscope in FIG. 1.

As a result, fluctuations in a quantity of emitted fluorescence from the fluorescent body 36 may occur. For example, FIG. 3 is a graph showing chronological fluctuations in a quantity of light Q for radiated light (fluorescence) emitted from the fluorescent wheel 35 (the rotational body). Note that, in FIG. 3, a line indicated by reference symbol Out shows fluctuations in the quantity of light Q at a radiation position near an outer circumference of the fluorescent wheel 35 (the rotational body) (see reference symbol A in FIG. 2). Similarly, in FIG. 3, a line indicated by reference symbol In shows fluctuations in the quantity of light Q at a radiation position nearer to an inner circumference of the fluorescent wheel 35 (the rotational body) than the above radiation position near the outer circumference (see reference symbol B in FIG. 2).

As shown in FIG. 2, there is a tendency that, as for the rotational deflection of the fluorescent wheel 35 (the rotational body) in the direction of the arrow Y, an amount of deflection at the radiation position B near the inner circumference is smaller than an amount of deflection at the radiation position A near the outer circumference. In other words, it can be said that influence by the rotational deflection is less when the rotation radius of the fluorescent wheel 35 (the rotating body) is smaller.

From the above, it can be said that, as shown in FIG. 3, there is a tendency that, as for fluctuations in the quantity of light of the fluorescent wheel 35 (the rotational body) also, fluctuations in the quantity of light at the radiation position B near the inner circumference are smaller than fluctuations in the quantity of light (reference symbol Out) at the radiation position A near the outer circumference. However, since rotational speed (rω) is slower as the rotation radius of the fluorescent wheel 35 is smaller, deterioration of the fluorescent body 36 is larger relative to an outer side as the rotation radius is smaller and as the rotational speed (rω) is slower, if the quantity of excitation light from the illuminating portion is constant.

On the other hand, if an observation target object is at a relatively near position relative to the distal end face of the distal end portion 21 (at the time of so-called near-point observation), it is possible to perform the observation with a small quantity of light, and, therefore, it is common that the quantity of emitted excitation light of the semiconductor laser LD 38 is controlled to be small. On the other hand, since a larger quantity of light is required to perform clear observation as the observation target object is farther away from the distal end face of the distal end portion 21, it is common that control to increase the quantity of emitted excitation light of the semiconductor laser LD 38 is performed.

Therefore, in consideration of the above, for example, when the quantity of emitted excitation light of the semiconductor laser LD 38 is small (at the time of near-point observation), that is, in a state in which the semiconductor laser LD 38 is radiating excitation light the quantity of which is the first quantity of light (a small quantity of light), the light source control portion 31 performs control to change the radiation position in an inner-side radial direction with the rotational body rotational axis 34 as the center relative to a radiation position on the fluorescent body 36 at the time of radiating excitation light the quantity of which is the second quantity of light (a large quantity of light).

That is, since the position of radiating excitation light onto the fluorescent body 36 is set to a position near the inner side in the radial direction with the rotational body rotational axis 34 as the center when the quantity of emitted light is small, it is possible to obtain stable illuminating light with few fluctuations of the quantity of light. At this time, since the quantity of emitted light is the first quantity of light (the small quantity of light), it is possible to suppress deterioration of the fluorescent body 36.

In a common case, a fluctuating in the quantity of light tends to be prominent at the time of near-point observation. In the present embodiment, however, since the radiation position of excitation light is changed to be near the inner side in the radial direction of the fluorescent body 36 at the time of near-point observation, it is possible to suppress fluctuations in the quantity of light at the time of near-point observation.

Further, on the other hand, when the quantity of emitted excitation light of the semiconductor laser LD 38 is large (at the time of far-point observation), that is, in a state in which the semiconductor laser LD 38 is radiating excitation light the quantity of which is the second quantity of light (the large quantity of light), the light source control portion 31 performs control to change the radiation position in an outer-side radial direction with the rotational body rotational axis 34 as the center relative to a radiation position on the fluorescent body 36 at the time of radiating excitation light the quantity of which is the first quantity of light (the small quantity of light).

That is, since the position of radiating excitation light onto the fluorescent body 36 is set to a position near the outer side in the radial direction with the rotational body rotational axis 34 as the center when the quantity of emitted light is large, it is possible to perform radiation of a large quantity of light while preventing deterioration of the fluorescent body 36, and, therefore, it is possible to perform observation with a sufficient quantity of light even if an observation target is far away.

Note that, in the case of switching the quantity of emitted excitation light of the semiconductor laser LD 38, it is necessary to consider the following points for a timing of switching the quantity of light and a timing of changing the radiation position.

That is, for example, in the case of switching from the state in which the semiconductor laser LD 38 is radiating excitation light the quantity of which is the first quantity of light (the small quantity of light) (in a state at the time of near-point observation) to the state in which the semiconductor laser LD 38 is radiating excitation light the quantity of which is the second quantity of light (the large quantity of light) (in a state at the time of far-point observation), the position of radiating the excitation light is moved from an inner-side position to an outer-side position. In this case, control is such that change of the radiation position (change from the inner side to the outer side) is performed first, and, then, switching of the quantity of emitted light (switching from the first quantity of light (the small quantity of light) to the second quantity of light (the large quantity of light)) is performed. Here, for example, if the light quantity switching from the small quantity of light to the large quantity of light is performed first, the radiation of the second quantity of light (the large quantity of light) is performed for a position near the inner side of the fluorescent body 36, which causes the fluorescent body 36 to deteriorate. In order to avoid this, in the above case, change of the radiation position is performed first, and light quantity switching control is performed after the change of the radiation position is completed.

On the other hand, for example, in the case of switching from the state in which the semiconductor laser LD 38 is radiating excitation light the quantity of which is the second quantity of light (the large quantity of light) (the state at the time of far-point observation) to the state in which the semiconductor laser LD 38 is radiating excitation light the quantity of which is the first quantity of light (the small quantity of light) (the state at the time of near-point observation), the position of radiating the excitation light is moved from the outer-side position to the inner-side position. In this case, control is such that switching of the quantity of emitted light (switching from the second quantity of light (the large quantity of light)) to the first quantity of light (the small quantity of light) is performed first, and, then, change of the radiation position (change from the outer side to the inner side) is performed. Here, for example, if the change of the radiation position from the outer side to the inner side of the fluorescent body 36 is performed first, the radiation of the second quantity of light (the large quantity of light) is performed for a position near the inner side of the fluorescent body 36, which causes the fluorescent body 36 to deteriorate. In order to avoid this, in the above case, switching of the quantity of light is performed first, and radiation position change control is performed after the switching of the quantity of light is completed.

Further, as for the quantity light switching timing and the radiation position changing timing, for example, control as below is also possible regardless of the examples described above. That is, the case of switching the quantity of light is, for example, the case of switching between the near-point observation state and the far-point observation state. In the case where light quantity switching control is performed as above, the control may be such that, irrespective of a quantity of radiated light at a current point of time, change of the radiation position is performed after switching the quantity of emitted light to the first quantity of light (the small quantity of light) or a small quantity of light equal to or smaller than a predetermined quantity of light once, and, after that, the quantity of light is switched to a quantity of light corresponding to the changed radiation position. In this case, since, when the radiation position is changed, radiation of the first quantity of light (the small quantity of light) is performed irrespective of the radiation position at the point of time before the change, it is possible to suppress damage to the fluorescent body 36 as far as possible.

Figure 4:
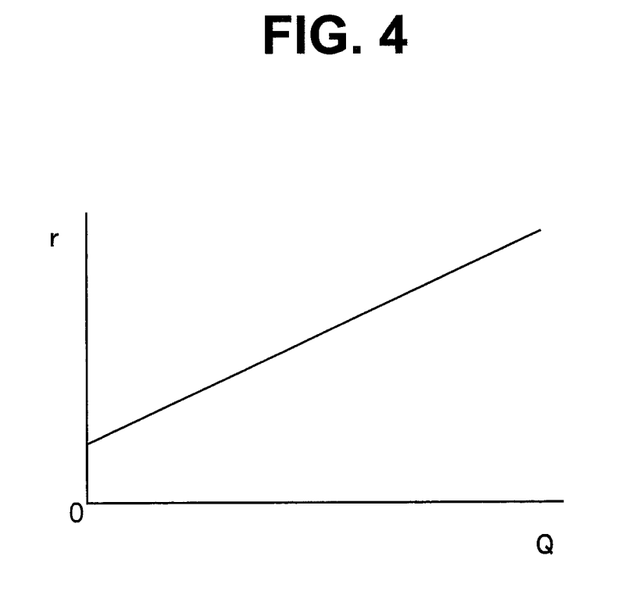
FIG. 4 is a graph showing a relationship between a radiation position of excitation light in a radial direction of a fluorescent body and a quantity of emitted excitation light in the light source device for endoscope in FIG. 1.

FIG. 4 is a graph showing a relationship between a radiation position (reference symbol r) of excitation light in the radial direction of the fluorescent body 36 and a quantity of emitted excitation light (reference symbol Q) in the case of performing such control as described above.

As shown in FIG. 4, the control can be performed so that, as the quantity of emitted excitation light Q increases, the radiation position r of excitation light is on the outer side in the radial direction. Note that, in the example shown in FIG. 4, an example is shown in which control is performed so that the quantity of excitation light gradually increases. As described above, it is only required that the quantity of excitation light can be selectively switched at least between the two stages of the first quantity of light and the second quantity of light. In that case (in the case of the two-stage light quantity switching), a certain quantity of light is specified so that control to cause the radiation position to move if the specified quantity of light is exceeded can be performed.

At the time of performing such control as described above in the light source unit 12 of the present embodiment, the quantity of emitted excitation light of the semiconductor laser LD 38 is detected with the optical sensor 45 first. A result of the detection is sent to the light source control portion 31. On receiving the detection result, the light source control portion 31 performs drive control of the rotational body shifting mechanism 39 via the rotational body driving portion 32 to change the radiation position of radiated light from the semiconductor laser LD 38 to be radiated onto the fluorescent body 36 of the fluorescent wheel 35.

Here, if the result of the detection by the optical sensor 45 is, for example, the first quantity of light (the small quantity of light), the light source control portion 31 drive-controls the rotational body shifting mechanism 39 via the rotational body driving portion 32 to cause the above rotational body unit (33, 34, 35 and 36) to be shifted and moved in the inner-side direction in the radial direction orthogonal to the axial direction of the rotational body rotational axis 34.

Further, similarly, if the result of the detection by the optical sensor 45 is, for example, the second quantity of light (the large quantity of light), the light source control portion 31 drive-controls the rotational body shifting mechanism 39 via the rotational body driving portion 32 to cause the above rotational body unit (33, 34, 35 and 36) to be shifted and moved in the outer-side direction in the radial direction orthogonal to the axial direction of the rotational body rotational axis 34.

Thereby, at the time of near-point observation for which the quantity of light is small, it is possible to suppress deterioration of the fluorescent body 36 while suppressing light quantity fluctuations by changing the radiation position to the inner side. On the other hand, at the time of far-point observation for which the quantity of light is large, it is possible to suppress deterioration of the fluorescent body 36 by changing the radiation position to the outer side.

Note that, though the optical sensor 45 in the above first embodiment is a detector configured to detect the quantity of emitted light from the semiconductor laser LD 38, the optical sensor 45 is not limited to the example. For example, the optical sensor 45 may be configured as a detector configured to detect a quantity of fluorescence from the fluorescent body 36. In that case also, the result of the detection by the optical sensor 45 is similarly outputted to the light source control portion 31 and used to drive-control the rotational body driving portion 32.

Further, though the above first embodiment exemplifies a configuration in which the endoscope system 1 causes only one kind of emitted light flux, for example, one kind of white fluorescence as an example of illuminating light emitted from the optical unit 40, the endoscope system 1 is not limited to the example. For example, as another form, a configuration is also possible in which a plurality of illuminating lights in different wavelength ranges can be switched and emitted. In that case, the configuration can be easily realized, for example, by providing a mechanism configured to change and switch illuminating light emitted from the above optical unit 40 to illuminating light in a different wavelength range, between the optical unit 40 and a proximal end of the light guide 26 connected to the connector portion 3b. As such a mechanism, that is, the configuration for converting illuminating light to illuminating light in a different wavelength range, a configuration already put to practical use in a light source device of an endoscope system which has been conventionally and commonly spread can be applied.

Furthermore, though the light source control portion 31 performs control to change the radiation position of excitation light in the radial direction of the fluorescent body 36 by causing the above rotational body unit (33, 34, 35 and 36) to shift and move in the direction orthogonal to the axial direction of the rotational body rotational axis 34 by the rotational body shifting mechanism 39 in the above first embodiment, the light source control portion 31 is not limited to the form example. As another form example, for example, an illuminating portion moving mechanism (not shown) configured to enable the above LD unit (37 and the LD 38) and the above optical unit 40 (41, 42, 43 and 44) to move in the radial direction relative to the fluorescent body 36 of the fluorescent wheel 35 (the rotational body) may be provided, and the light source control portion 31 may be configured to cause the illuminating portion moving mechanism, instead of the above rotational body shifting mechanism 39, to be driven by control almost similar to the control of the above first embodiment.

As described above, according to the above first embodiment, the optical sensor 45 configured to detect a quantity of emitted light of the semiconductor laser LD 38 or the fluorescent body 36 and the rotational body shifting mechanism 39 configured to cause the rotational body unit (33, 34, 35 and 36) to shift and move in the direction orthogonal to the axial direction of the rotational body rotational axis 34 are provided, and a configuration is made so that control is performed to change the radiation position of excitation light in the radial direction of the fluorescent body 36 according to the quantity of emitted light of the semiconductor laser LD 38 or the fluorescent body 36.

In this case, in the state in which the quantity of excitation light is the first quantity of light (the small quantity of light), control is performed to change the position of radiating the excitation light to the fluorescent body 36 to the inner side in the radial direction of the fluorescent wheel 35 with the rotational body rotational axis 34 as the center.

On the other hand, in the state in which the quantity of excitation light is the second quantity of light (the large quantity of light), control is performed to change the position of radiating the excitation light to the fluorescent body 36 to the outer side in the radial direction of the fluorescent wheel 35 with the rotational body rotational axis 34 as the center.

By such a configuration, it is possible to, in the light source unit 12 (the light source device for endoscope) provided with the fluorescent wheel 35 (the rotational body), which is provided with the fluorescent body 36, and the semiconductor laser LD 38 (the illuminating portion), prevent influence of light quantity fluctuations which occur due to the rotation mechanism of the fluorescent wheel 35 (the rotational body) and supply stable illuminating light with few light quantity fluctuations to the endoscope 2, and, at the same time, it is possible to suppress deterioration of the fluorescent body 36. Especially, at the time of near-point observation in which light quantity fluctuations tend to be prominent, it is possible to suppress deterioration of the fluorescent body 36 while preventing the light quantity fluctuations.

Second Embodiment

Next, a second embodiment of the present invention will be described below. A basic configuration of the present embodiment is almost similar to the configuration of the first embodiment described above. In the present embodiment, instead of providing the optical sensor 45 configured to detect a quantity of emitted light of the semiconductor laser LD 38 or the fluorescent body 36, a quantity of emitted light is estimated from a making current to the semiconductor laser LD 38 (the illuminating portion), and control similar to the control of the first embodiment described above, that is, control to change the position of radiating excitation light to the fluorescent body 36 in the radial direction is performed. Therefore, the basic configuration of the present embodiment is almost similar to the configuration of the first embodiment described above.

Figure 5:
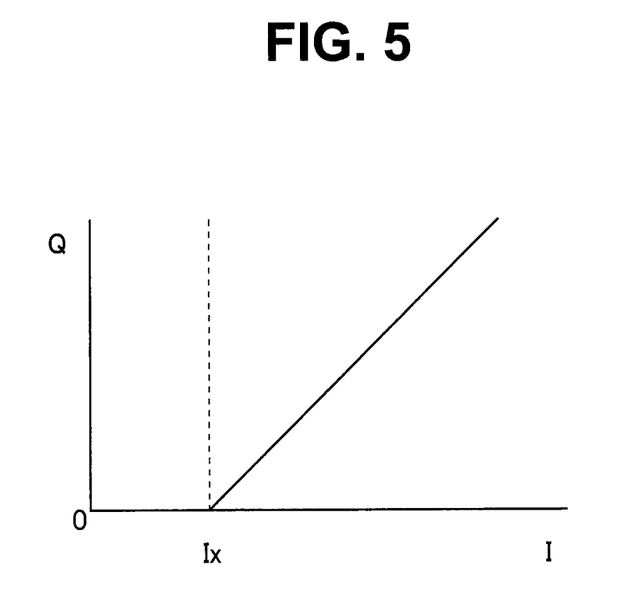
Figure 6:
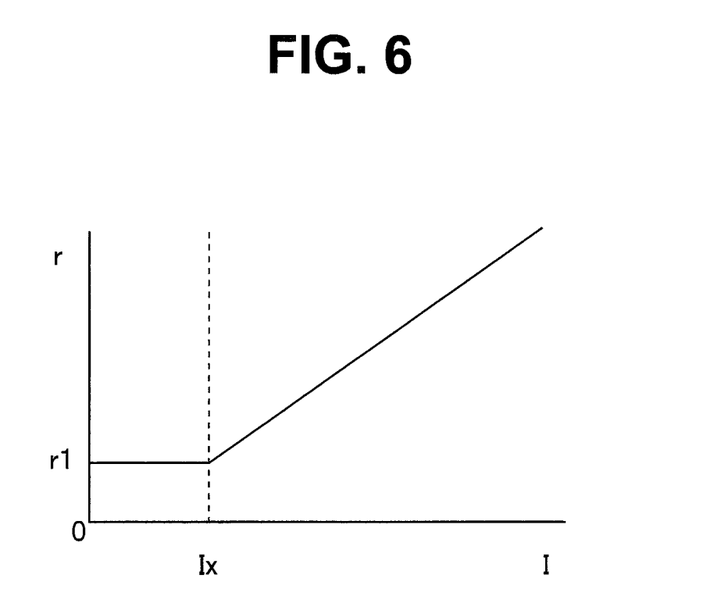
FIG. 6 is a graph showing a relationship between the making current (I) to the semiconductor laser LD (the illuminating portion) and a radiation position (r) in the light source device for endoscope of the second embodiment of the present invention.

FIG. 5 is a graph showing a relationship between a making current (I) to the semiconductor laser LD 38 (the illuminating portion) and an emitted quantity of excitation light (Q) in a light source device for endoscope of the present embodiment. Further, FIG. 6 is a graph showing a relationship between the making current (I) to the semiconductor laser LD 38 (the illuminating portion) and a radiation position (r) in the light source device for endoscope of the present embodiment. Note that broken lines in FIGS. 5 and 6 indicate a smallest current value at which emission of the semiconductor laser LD (the illuminating portion) 38 is started.

In the light source device for endoscope of the present embodiment, as shown in FIG. 5, emission is started, for example, when the making current I to the semiconductor laser LD (the illuminating portion) 38 exceeds a predetermined value Ix. Then, as the making current I increases, the quantity of emitted excitation light Q increases.

Further, as shown in FIG. 6, in the light source device for endoscope of the present embodiment, for example, the position (r) in the radial direction of the fluorescent body 36 corresponding to a light source position at which emission of the making current I to the semiconductor laser LD (the illuminating portion) 38 is started at the predetermined value Ix is set to a position (r1) near the inner side of the fluorescent wheel 35 with the rotational body rotational axis 34 as the center, and control is performed so that, as the making current I to the semiconductor laser LD (the illuminating portion) 38 increases, the position (r) of radiation to the fluorescent body 36 comes near the outside in the radial direction.

By the present embodiment configured as above, effects similar to the effects of the first embodiment described above can be also obtained, and electrical parts such as an optical sensor and circuit configurations related to the electrical parts can be omitted. It is possible to contribute to configuration simplification more.

Third Embodiment

Next, a third embodiment of the present invention will be described below. A basic configuration of the present embodiment is almost similar to the configurations of the first and second embodiments described above. In the present embodiment, as explicit observation operation mode for the user, at least two modes, for example, a light quantity priority mode suitable at the time of far-point observation and a light quantity fluctuation suppression mode suitable at the time of near-point observation are provided. The user appropriately switches to one of the prepared observation operation modes by a manual selection operation according to a use situation using an operation member (not shown) of the operation panel 14.

Note that, here, the radiation position is set to a position near the outer side in the radial direction of the fluorescent body 36 in the above light quantity priority mode. Further, the radiation position is set to a position near the inner side in the radial direction of the fluorescent body 36 in the above light quantity fluctuation suppression mode.

Thus, the basic configuration of the present embodiment is almost similar to the configurations of the first and second embodiments described above. Further, in the present embodiment also, such a form may be adopted that, instead of the optical sensor of the above first embodiment, the control (the control of a making current to the illumination portion) shown in the above second embodiment is performed.

Further, in the light source device for endoscope of the present embodiment, such a configuration may be added that various kinds of pieces of information about an endoscope used, being connected to the light source device, such as a scope ID, are read, and a quantity of emitted excitation light suitable for the connected endoscope and an area of radiation to the fluorescent body 36 in the radial direction are automatically set. In this case also, control to change the position of radiation to the fluorescent body 36 in the radial direction may be automatically performed according to quantities of light corresponding to normal observation modes, such as a far-point observation mode and a near-point observation mode. In this case, for example, such a configuration is conceivable that, when the user performs an operation of selecting one of the far-point observation mode and the near-point observation mode, a quantity of excitation light and a radiation position are automatically set according to the switching to the mode.

Note that, as an example of the various kinds of pieces of information about the endoscope connected and used, a scope ID is described. As information included in the scope ID, there are various pieces of information, for example, a kind of scope (a kind of use with regard to a site to be observed, for example, for stomach observation, for esophagus observation, for large intestine observation or the like), a kind of used image pickup device (for example, CCD, CMOS or the like) and a kind of illuminating light source.

Further, though the operation mode switching operation is described as an example of a manual operation by the user, the manual operation is not limited to the operation mode switching operation. For example, a form is also possible in which the user can perform an operation for changing the position of radiating excitation light to the fluorescent body 36 by the operation member. In this case, control is performed so that excitation light is emitted with a quantity of light corresponding to a radiation position specified by a change instruction, by the operation of the operation member of the operation panel 14, and, thereby, change of the quantity of light is performed. In such a form also, effects similar to the effects of each embodiment described above can be obtained.

Note that the present invention is not limited to the embodiments described above, and it is, of course, possible to perform various modifications and applications within a range not departing from the spirit of the invention. Furthermore, the above embodiments include inventions at various stages, and various inventions can be extracted by appropriate combinations among a plurality of disclosed constituent features. For example, even if some constituent features are deleted from all constituent features shown in one of the above embodiments, a configuration obtained after deleting the constituent features can be extracted as an invention if the problem to be solved by the invention can be solved, and the advantageous effects of the invention can be obtained. Furthermore, components among different embodiments may be appropriately combined. The present invention is only limited by accompanying claims and not restricted by particular practiced aspects of the claims.

INDUSTRIAL APPLICABILITY

The present invention can be applied not only to an endoscope control apparatus in the medical field but also to an endoscope control apparatus in the industrial field.

What is claimed is:

1. A light source device for endoscope comprising:
   a rotational body configured to rotate with a rotational axis as a center;
   a fluorescent material arranged in an area on the rotational body, the area having a predetermined radius with the rotational axis as a center, the fluorescent material being configured to generate fluorescence by excitation light being radiated;
   an illuminating light source configured to selectively radiate excitation light a quantity of which is a first quantity of light and excitation light a quantity of which is a second quantity of light which is a quantity of light larger than the first quantity of light to the fluorescent material; and
   a controller configured to:
      control a radiation position to which the excitation light is radiated so as to switch between a first state of radiating the excitation light the quantity of which is the first quantity of light to the fluorescent material arranged in an area having a first radius from the rotational axis and a second state of radiating the excitation light the quantity of which is the second quantity of light to the fluorescent material arranged in an area having a second radius from the rotational axis that is greater than the first radius; and
      select the first state in a light quantity fluctuation suppression mode and select the second state in a light quantity priority mode, where the light quantity fluctuation suppression mode is configured for near-point observation and the light quantity priority mode is configured for far-point observation.

2. The light source device for endoscope according to claim 1, wherein the controller controls the radiation position by causing the rotational body or the illumination light source to move.

3. The light source device for endoscope according to claim 2, the controller is configured to move the rotational body in a radial direction with the rotational axis as the center to change the radiation position of the excitation light on the fluorescent material.

4. The light source device for endoscope according to claim 2, wherein the controller is configured to move the illuminating light source in the radial direction of the rotational body with the rotational axis as the center to change the radiation position of the excitation light on the fluorescent material.

5. The light source device for endoscope according to claim 2, wherein the controller is further configured to receive an instruction signal for changing the radiation position of the excitation light on the fluorescent material in the radial direction of the rotational body with the rotational axis as the center; and
   control the illuminating light source so that a quantity of excitation light corresponding to the instructed radiation position is emitted.

6. The light source device for endoscope according to claim 1, wherein the controller is further configured to:
   receive a control signal for controlling a quantity of the excitation light the illuminating light source radiates; and
   change the radiation position of the excitation light on the fluorescent material based on the control signal.

7. The light source device for endoscope according to claim 1, wherein the controller is further configured to:
   receive a detection result of a quantity of emitted fluorescence the fluorescent material generates or of the excitation light; and
   change the radiation position of the excitation light on the fluorescent material based on the detection result.

8. The light source device for endoscope according to claim 1, wherein, when, the controller switches from the second quantity of light to the first quantity of light, the controller changes the radiation position to an inner side in the radial direction with the rotational axis as the center, relative to the radiation position at the time of radiating the excitation light the quantity of which is the second quantity of light.

9. The light source device for endoscope according to claim 1, wherein, when the controller switches from the first quantity of light to the second quantity of light, the controller changes the radiation position to an outer side in the radial direction with the rotational axis as the center, relative to the radiation position at the time of radiating the excitation light the quantity of which is the first quantity of light.

10. The light source device for endoscope according to claim 1, wherein, when the controller switches to the first quantity of light, and, after changing the radiation position of the excitation light, switches to a quantity of light corresponding to the changed radiation position.

11. An endoscope system comprising:
   the light source device according to claim 1; and
   an endoscope operatively connected to the light source device.

* * * * *